(12) United States Patent
Moore et al.

(10) Patent No.: US 11,051,799 B2
(45) Date of Patent: Jul. 6, 2021

(54) AUGMENTED SUTURE CONSTRUCT FOR SYNDESMOTIC STABILIZATION

(71) Applicant: Wright Medical Technology, Inc., Memphis, TN (US)

(72) Inventors: Jesse G. Moore, Germantown, TN (US); Bryan D. Den Hartog, St. Paul, MN (US); Gregory C. Berlet, Westerville, OH (US); Murray John Penner, Vancouver (CA); Bruce E. Cohen, Charlotte, NC (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 120 days.

(21) Appl. No.: 16/044,689

(22) Filed: Jul. 25, 2018

(65) Prior Publication Data

US 2019/0069890 A1    Mar. 7, 2019

Related U.S. Application Data

(60) Provisional application No. 62/553,410, filed on Sep. 1, 2017.

(51) Int. Cl.
*A61B 17/04* (2006.01)
*A61B 17/80* (2006.01)
(Continued)

(52) U.S. Cl.
CPC ........ *A61B 17/0401* (2013.01); *A61B 17/683* (2013.01); *A61B 17/8061* (2013.01);
(Continued)

(58) Field of Classification Search
CPC ... A61B 17/0401; A61B 17/683; A61B 17/80; A61B 17/8038; A61B 17/82;
(Continued)

(56) References Cited

U.S. PATENT DOCUMENTS 5,921,986 A * 7/1999 Bonutti .............. A61B 17/0401
606/215
7,235,091 B2    6/2007 Thornes
(Continued)

FOREIGN PATENT DOCUMENTS

WO    2005041823    5/2005

OTHER PUBLICATIONS

Zhan, et al., Anterior-Inferior Tibiofibular Ligament Anatomical Repair and Augmentation Versus Trans-Syndesmosis Screw Fixation for the Syndesmotic Instability in External-Rotation Type Ankle Fracture with Posterior Malleolus Involvement: A prospective and comparative study, Injury, Apr. 14, 2016, 7 Pages.
(Continued)

*Primary Examiner* — Robert A Lynch
(74) *Attorney, Agent, or Firm* — Duane Morris LLP (57) ABSTRACT

A method includes forming a bone tunnel through a first bone and a second bone and inserting a flexible construct through the bone tunnel. The flexible construct includes a first anchoring element and a second anchoring element coupled by at least one flexible strand defining an adjustable loop. The at least one flexible strand includes a first end extending from the first anchoring element in an opposite direction from the adjustable loop. A length of the adjustable loop is adjusted to position the first bone and the second bone in a selected spacing. The first end of the at least one flexible strand is coupled to a tissue section using a third anchoring element.

10 Claims, 10 Drawing Sheets

(51) Int. Cl.
*A61B 17/68* (2006.01)
*A61B 17/86* (2006.01)
*A61B 17/84* (2006.01)

(52) U.S. Cl.
CPC ............. *A61B 17/842* (2013.01); *A61B 17/86* (2013.01); *A61B 2017/0403* (2013.01); *A61B 2017/044* (2013.01); *A61B 2017/0404* (2013.01); *A61B 2017/0412* (2013.01); *A61B 2017/0417* (2013.01); *A61B 2017/0458* (2013.01)

(58) Field of Classification Search
CPC .......... A61B 17/842; A61B 2017/0403; A61B 2017/0404; A61B 2017/0414; A61B 2017/044; A61B 2017/0445; A61B 2017/0446; A61B 2017/0448; A61B 2017/045; A61B 2017/0456; A61B 2017/0458

See application file for complete search history.

(56) References Cited

U.S. PATENT DOCUMENTS

| | | | |
|---|---|---|---|
| 7,326,211 | B2 | 2/2008 | Padget et al. |
| 7,578,825 | B2 | 8/2009 | Huebner |
| 7,585,311 | B2 | 9/2009 | Green et al. |
| 7,625,395 | B2 | 12/2009 | Muckter |
| 8,100,942 | B1 | 1/2012 | Green et al. |
| 8,109,969 | B1 | 2/2012 | Green et al. |
| 8,118,835 | B2 | 2/2012 | Weisel et al. |
| 8,231,674 | B2 | 7/2012 | Albertorio et al. |
| 8,398,678 | B2 | 3/2013 | Baker et al. |
| 8,465,522 | B2 | 6/2013 | Burkhart |
| 8,506,597 | B2 | 8/2013 | Kaiser et al. |
| 8,771,351 | B2 | 7/2014 | Elatrache et al. |
| 8,814,904 | B2 | 8/2014 | Bennett |
| 8,845,686 | B2 | 9/2014 | Bennett |
| 9,005,285 | B2 | 4/2015 | Niu et al. |
| 9,101,355 | B2 | 8/2015 | Lantz et al. |
| 9,131,937 | B2 | 9/2015 | Chan et al. |
| 9,138,219 | B2 | 9/2015 | Horrell et al. |
| 9,149,268 | B2 | 10/2015 | Graul et al. |
| 9,179,905 | B2 | 11/2015 | Pamichev et al. |
| 9,445,827 | B2 | 9/2016 | Kaiser et al. |
| 2004/0127907 | A1* | 7/2004 | Dakin .................. A61B 17/842 606/62 |
| 2008/0071299 | A1 | 3/2008 | Allinniemi et al. |
| 2009/0054982 | A1 | 2/2009 | Cimino |
| 2009/0228049 | A1 | 9/2009 | Park |
| 2013/0158601 | A1* | 6/2013 | Stone ................. A61B 17/0401 606/232 |
| 2015/0032157 | A1 | 1/2015 | Dooney, Jr. et al. |
| 2015/0039029 | A1 | 2/2015 | Wade |
| 2015/0051601 | A1* | 2/2015 | Larsen ................... A61B 17/82 606/74 |
| 2016/0030035 | A1 | 2/2016 | Zajac et al. |
| 2016/0038201 | A1 | 2/2016 | Cummings |
| 2016/0089131 | A1 | 3/2016 | Wade |
| 2016/0089189 | A1 | 3/2016 | Buscaglia et al. |
| 2016/0113691 | A1 | 4/2016 | Fritzinger et al. |
| 2016/0262814 | A1 | 9/2016 | Wainscott |
| 2016/0278828 | A1 | 9/2016 | Ragghianti |
| 2016/0287302 | A1 | 10/2016 | Horrell et al. |
| 2016/0354197 | A1 | 12/2016 | Roller et al. |
| 2017/0049434 | A1* | 2/2017 | Dooney, Jr. ......... A61B 17/0485 |
| 2018/0000476 | A1* | 1/2018 | Spenciner .......... A61B 17/0401 |

OTHER PUBLICATIONS

Wright Medical Technology, Inc., Gravity, Syndesmosis LP, Alpha Surgical Technique, Jan. 5, 2017.

Porter, et al. "Optimal Management of Ankle Syndesmosis Injuries", Open Access Journal of Sports Medicine, Aug. 5, 2014.

Zimmer Biomet, "ZipTight Ankle Fixation System", https://www.zimmerbiomet.com/medical-professionals/foot-and-ankle/product/ziptight-fixation-system.html, retrieved from the Internet on Jul. 9, 2018.

Arthrex, "Knotless Tightrope Syndemosis Fixation", Surgical Technique, Jan. 1, 2015.

Clanton, et al., "Biomechanical Comparison of 3 Current Ankle Syndesmosis Repair Techniques", American Orthopaedic Foot & Ankle Society, Oct. 3, 2016.

Downey, et al., "Syndemosis Injury with Concomitant Deltoid Disruption in a Trimalleolar Equivalent Ankle Fracture: A Case Report", SciMedCentral, Annals of Sports Medicine and Research, Nov. 16, 2015.

* cited by examiner

AUGMENTED SUTURE CONSTRUCT FOR SYNDESMOTIC STABILIZATION

CROSS-REFERENCE TO RELATED APPLICATIONS

This application claims benefit of U.S. Provisional Application Ser. No. 62/553,410, filed on Sep. 1, 2017, entitled "AUGMENTED SUTURE CONSTRUCT FOR SYNDESMOTIC STABILIZATION," which is incorporated by reference herein in its entirety.

BACKGROUND

Various injuries include separation of soft tissue from one or more bones and/or separation of bones from normally anatomical correct positioning. Maintaining the bones in the correct anatomical positions during healing is important to provide proper soft tissue reattachment and proper bone healing. For example, during syndesmosis repair, current systems maintain a first bone and a second bone in a fixed position to allow the connective tissue to refuse.

Fixation of a first bone and a second bone can allow some connective tissue to refuse, but not all. Connective tissue that is partially and/or completely separated from the first bone and/or the second bone may not reconnect and/or may reconnect in an undesirable and/or loose location. Failure to properly position tissue during a syndesmosis procedure can lead to additional surgeries or failure of the syndesmotic correction.

SUMMARY

In various embodiments, a method is disclosed. The method includes a step of forming a bone tunnel through a first bone and a second bone. A flexible construct is inserted through the bone tunnel. The flexible construct includes a first anchoring element and a second anchoring element coupled by at least one flexible strand defining an adjustable loop. The at least one flexible strand including a first end extending from the first anchoring element in an opposite direction from the adjustable loop. A length of the adjustable loop is adjusted to position the first bone and the second bone in a selected spacing. The first end of the at least one flexible strand is coupled to a tissue section using a third anchoring element.

In various embodiments, an anchoring system is disclosed. The anchoring system includes an anchoring construct and a tissue anchor. The anchoring construct includes a first anchor, a second anchor, and a first flexible strand defining an adjustable loop extending between the first anchor and the second anchor. The first flexible strand has a first end extending away from the first and second anchors. The tissue anchor is coupled the first end of the flexible strand and is configured to couple the first end of the flexible strand to a first tissue section.

In various embodiments, a system is disclosed. The system includes a bone plate having a body extending between a bone facing surface and an opposing surface. The body defines a hole sized and configured to receive a portion of a flexible construct therethrough. The system further includes a flexible strand coupled to the bone plate at a first end and a tissue anchor coupled to a second end of the flexible strand. The tissue anchor is configured to couple the flexible strand to a tissue section.

BRIEF DESCRIPTION OF DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. As used herein, proximal/distal refers to a relationship between an identified element (such as a surgical instrument) and a user (e.g., a surgeon) grasping or manipulating the identified element.

In various embodiments, an anchoring construct for syndesmotic repair is disclosed. The anchoring construct includes a bone plate coupled to a first bone. The bone plate defines a first hole extending therethrough. A flexible strand is coupled to the bone plate. The flexible strand can be looped through the first hole and/or anchored to the bone plate by an anchoring element (such as a knot capsule, a button, a screw, and/or any other suitable anchoring element). The flexible strand extends from the bone plate to a tissue anchor. The tissue anchor is configured to be coupled to a tissue section remote from the first bone, such as a second bone, a spaced apart section of the first bone, and/or soft-tissue. A length of an intermediate portion of the flexible strand extending from the bone plate to the tissue anchor is adjustable to maintain a selected spacing between the first bone and the remote tissue section. The anchoring construct maintains the first bone and the second bone in a constrained position allowing a predetermined amount of motion (such as 0-5 mm) while maintaining the first and second bone in a suitable position for soft tissue reattachment and repair.

In various embodiments, a system for syndesmotic repair is disclosed. The system includes a flexible construct having at least one adjustable loop defined by a first flexible strand. The adjustable loop is configured to extend through a bone tunnel defined in a first bone and a second bone. A first anchor is positioned at a first end of the adjustable loop and is configured to anchor the adjustable loop to the first bone. The first anchor can include a knot capsule, a bone plate, a flat button, screw and/or any other suitable anchoring element. The second end of the adjustable loop is coupled to the second bone by a second anchoring element. The second anchoring element can include a knot capsule, a flat button, a screw, and/or any other suitable anchoring element. The adjustable loop can be shortened to maintain the first bone and the second bone at a select spacing. A second flexible strand extends from the first anchoring element and is coupled to a tissue anchor. The tissue anchor is configured couple the second flexible strand to a tissue section remote from the first anchoring element, such as the first bone, the second bone, and/or a soft tissue section. An intermediate portion of the second flexible strand is adjustable and is configured to maintain a selected spacing between the first anchor and the remote tissue section. The tissue anchor can be configured to further anchor the second flexible strand to one of the first bone or the second bone.

Figure 1:
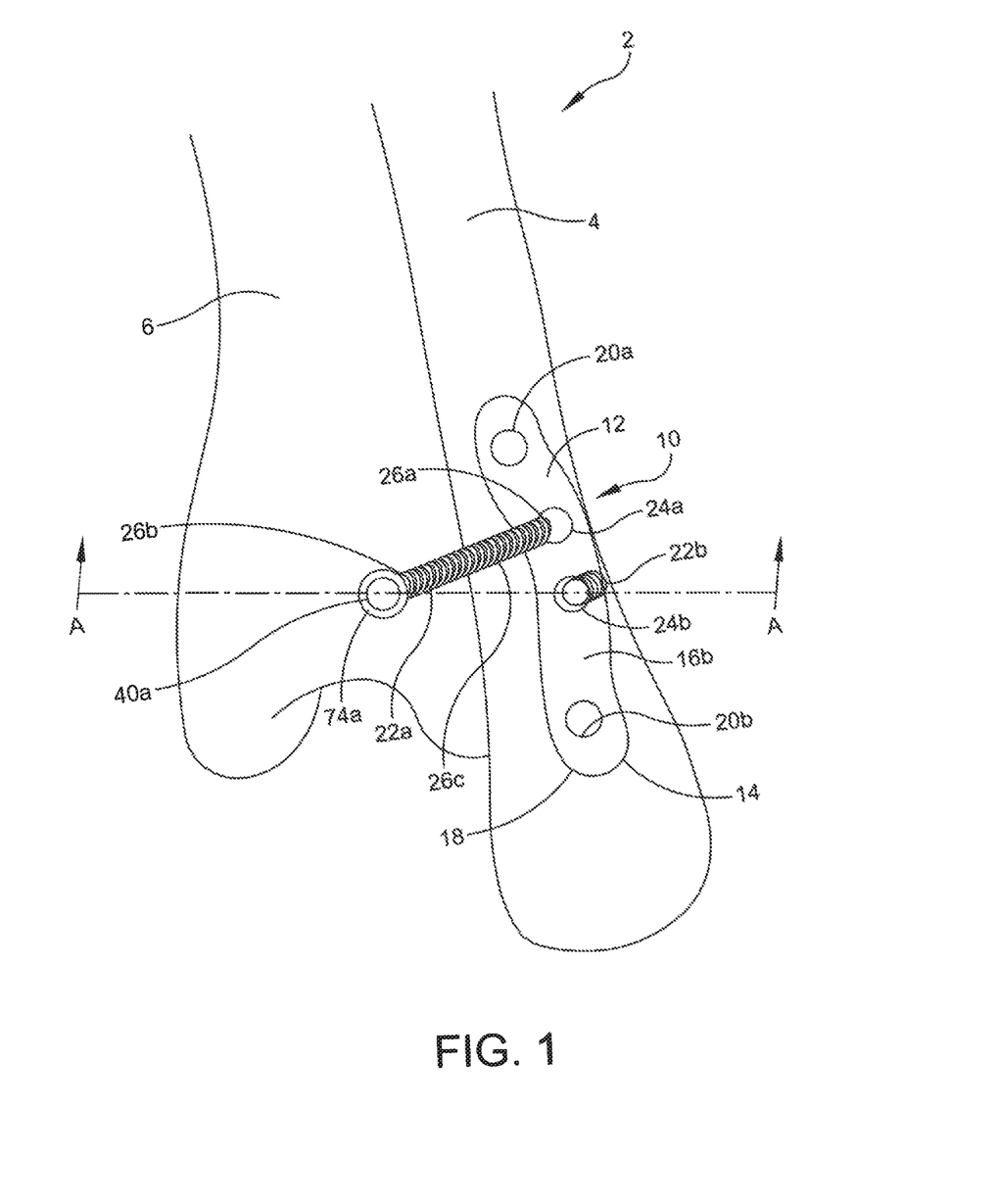
FIG. 1 illustrates an anchoring construct coupled to a first bone and a second bone, in accordance with some embodiments.
Figure 2:
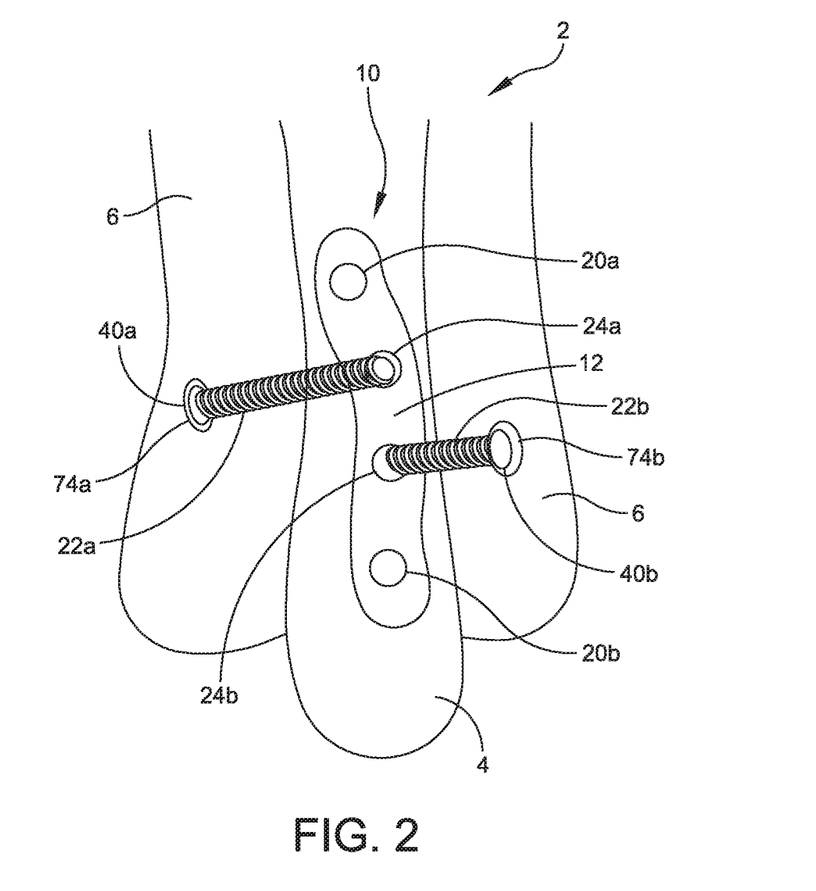
FIG. 2 illustrates a front view of the anchoring construct of FIG. 1, in accordance with some embodiments.
Figure 3:
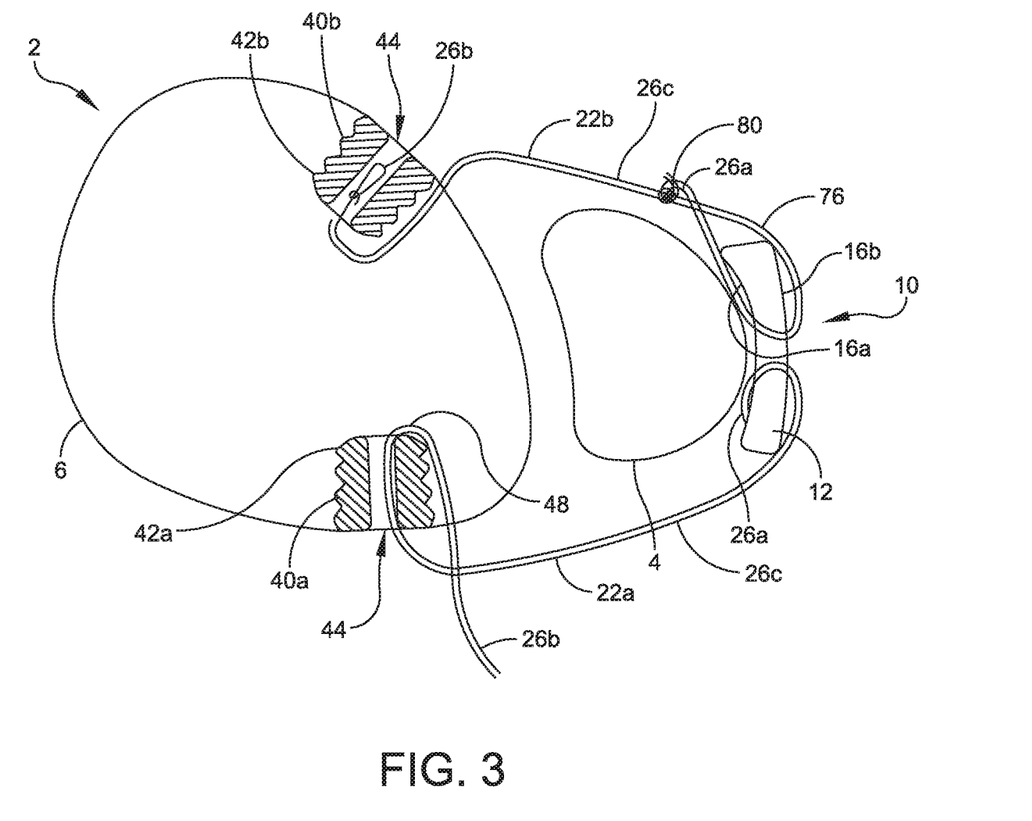
FIG. 3 illustrates a cross-section taken along line A-A in FIG. 1, in accordance with some embodiments.

FIGS. 1-3 illustrate a surgical site 2 including a first bone 4 and a second bone 6 coupled by an anchoring construct 10, in accordance with some embodiments. The anchoring construct 10 is configured to maintain the first bone 4 and the second bone 6 at a selected spacing. As a non-limiting example, in some embodiments, the first bone 4 is a fibula and the second bone 6 is a tibia. The anchoring system 10 includes a bone plate 12 configured to be coupled the first bone 4. The bone plate 12 includes a body 14 extending between a bone contacting surface 16a and an opposed surface 16b. The body 14 is further defined by a sidewall 18 defining a perimeter of the bone plate 12 and extending between the bone contacting surface 16a and the opposed surface 16b. In some embodiments, the body 14 defines one or more fastener holes 20a, 20b extending from the opposed surface 16b to the bone contacting surface 16a. The fastener holes 20a, 20b are sized and configured to receive a fastener therein to couple the bone plate 12 to the first bone 4. For example, in various embodiments, the fastener holes 20a, 20b are sized and configured to receive a fastener, such as a screw, peg, pin, a knot capsule, and/or any other suitable fastener therein.

In some embodiments, at least one flexible strand 22a extends from the bone plate 12. In the illustrated embodiments, a first flexible strand 22a and a second flexible strand 22b extend from the bone plate 12. The flexible strands 22a, 22b can include any suitable material, such as sutures, ribbons, tape, threads, rope, and/or any other suitable material. A first end 26a of each of the flexible strands 22a, 22b extends through and/or is coupled to the bone plate 12. The flexible strands 22a, 22b each extend from the first end 26a to a second end 26b. The second end 26b is configured to be coupled to a tissue section that is remote from (e.g., spaced apart from) the bone plate 12.

In some embodiments, the first end 26a of a flexible strand 22b is passed around and therethrough the body 14 of the bone plate 12 to define a loop 76. For example, as illustrated in FIG. 3, the first end 26a of the second flexible strand 22b is passed through a first opening 24a formed in the bone plate 12 and coupled to an intermediate portion 26c of the second flexible strand 22b to define the loop 76. In some embodiments, the first end 26a is coupled to the intermediate portion 26c of the flexible strand 22b by a knot 80. The knot 80 can be any suitable knot, such as, for example, a slip-knot, a fixed knot, and/or any other suitable knot. In some embodiments, one or more of the flexible strands 22a, 22b are coupled to the bone plate 12 by an interference fit. For example, as illustrated in FIG. 3, the first end 26a of the first flexible strand 22a is positioned between a bone-facing surface 16a of the bone plate 12 and an outer surface of the first bone 4. The first end 26a of the first flexible strand 22a is maintained in a fixed position by an interference fit between a bone plate 12 and an outer surface of the first bone 4. Although specific embodiments are discussed herein, it will be appreciated that the flexible strands 22a, 22b can be coupled to the bone plate 12 using any suitable coupling mechanism, such as posts, knots, fastener, and/or any other suitable mechanism.

Figure 4:
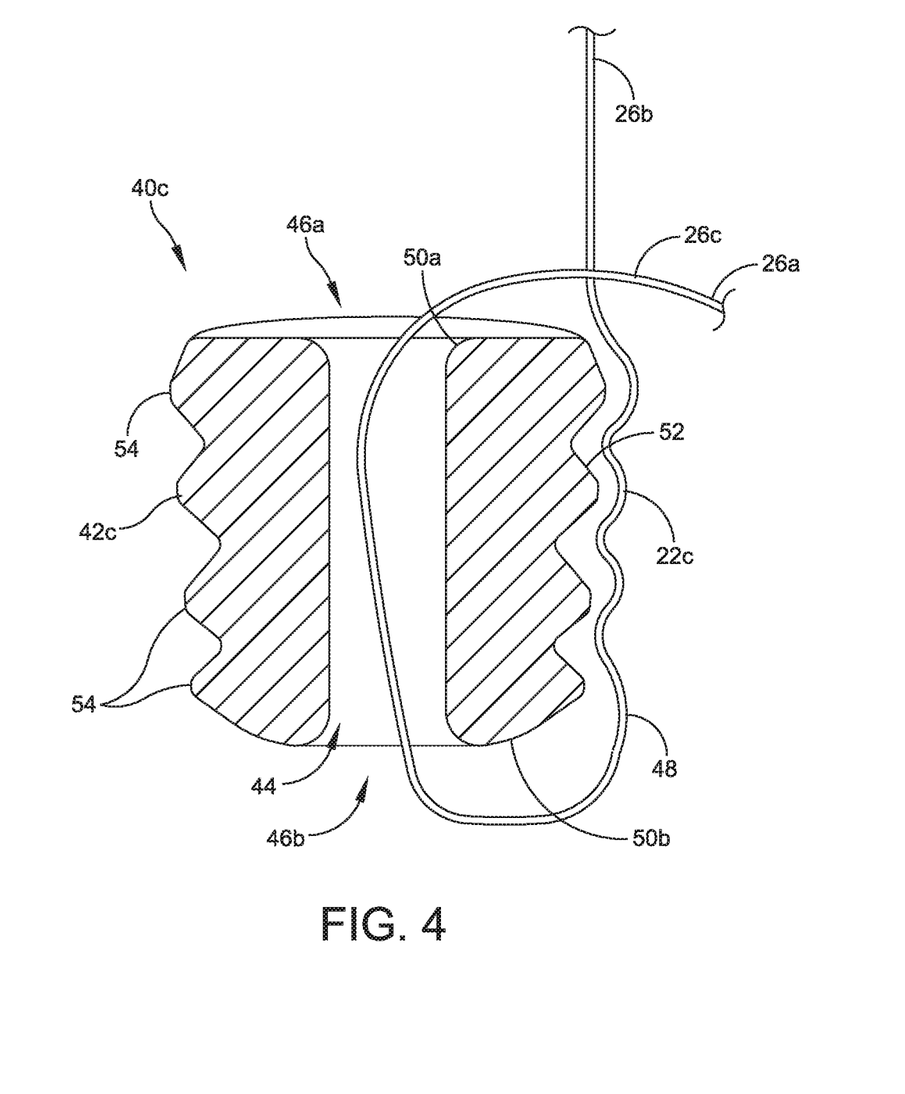
FIG. 4 illustrates a tissue anchor having a flexible strand looped through a channel, in accordance with some embodiments.
Figure 5:
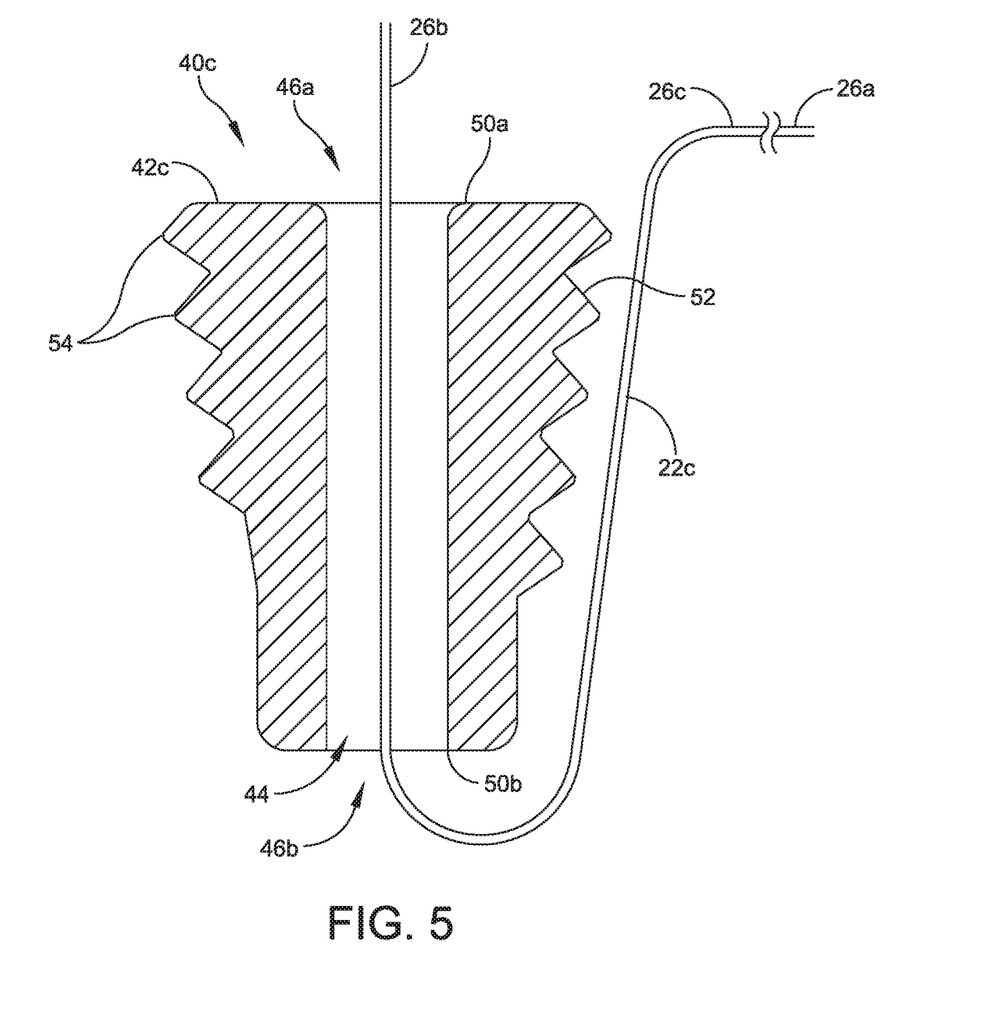
FIG. 5 illustrates a tissue anchor having a flexible strand passed through a channel, in accordance with some embodiments.
Figure 6:
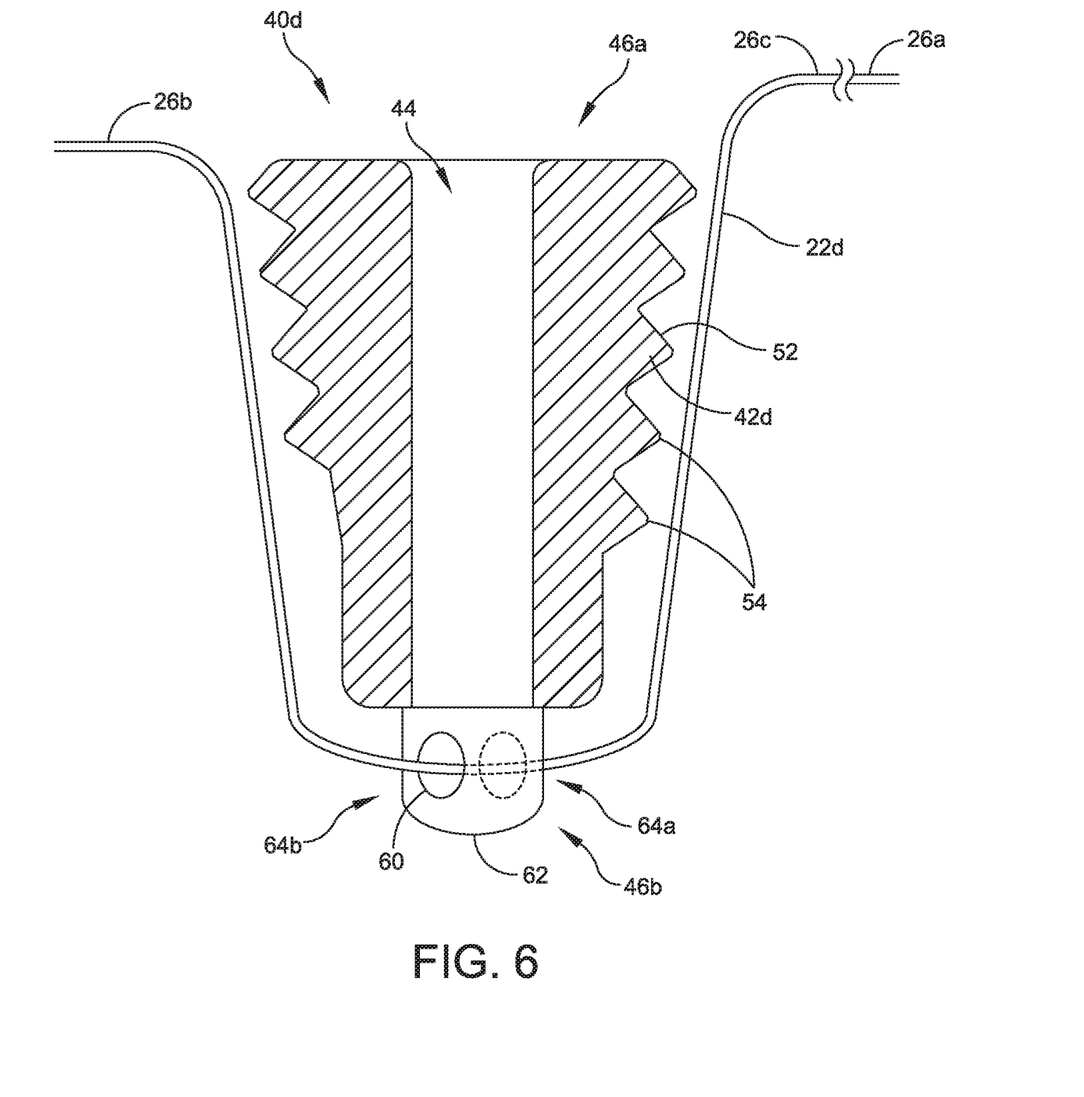
FIG. 6 illustrates a tissue anchor having an eyelet with a flexible strand extending therethrough, in accordance with some embodiments.

In some embodiments, the second end 26b of each of the flexible strands 22a, 22b configured to be coupled to a tissue section remote from the bone plate 12. For example, as best seen in FIG. 2, in some embodiments, the second end 26b of each of the flexible strands 22a, 22b is coupled to the second bone 6. The second end 26b of each of the flexible strands 22a, 22b is coupled to the second bone 6 by respective tissue anchors 40a, 40b. The tissue anchors 40a, 40b are inserted into respective anchor holes 74a, 74b formed in the second bone 6. The anchors 40a, 40b can be inserted through any suitable method, such as impaction, rotation, and/or any other suitable insertion method. Various embodiments of anchors are illustrated in FIGS. 4-6 and discussed in greater detail below. In other embodiments, the tissue anchors 40a, 40b are additionally and/or alternatively configured to couple the flexible strands 22a, 22b to soft tissue, such as connective tissue, ligaments, muscle, etc.

In some embodiments, an intermediate portion 26c of each of the flexible strands 22a, 22b extending between the bone plate 12 and the respective anchors 40a, 40b has an adjustable length. The bone plate 12 is coupled to the first bone 4 and the second end 26b of each of the flexible strands 22a, 22b is coupled to the second bone 6. The length of the intermediate portion 26c of the respective flexible strands 22a, 22b is adjusted to maintain the first bone 4 and the second bone 6 in a selected spacing. For example, in some embodiments, the flexible strands 22a, 22b each define an adjustable loop extending between the bone plate 12 and a respective tissue anchor 40a, 40b. In other embodiments, the flexible strands 22a, 22b are advanced through a hole 24a, 24b formed in the bone plate 12 and/or a channel 44 in the respective anchor 40a, 40b to decrease a length of an intermediate portion 26c of the flexible strand 22a, 22b extending between the bone plate 12 and the respective tissue anchor 40a, 40b. The intermediate portion 26c of each of the one or more flexible strands 22a, 22b is adjusted to maintain the first bone 4 and the second bone 6 in a selected position, such as a substantially anatomically correct position and/or to position soft tissue adjacent to one of the first bone 4 and/or the second bone 6.

In some embodiment, the first flexible strand 22a is maintained at a selected length by an interference fit between the second bone 6 and a body 42a of the first tissue anchor 40a. Similarly, the second flexible strand 22b is maintained at a selected length by an interference fit between the second bone 6 and a body 42b of the second tissue anchor 40b. The flexible strands 22a, 22b are positioned between respective anchors 40a, 40b and an inner surface 72 of a respective anchor hole 74a, 74b formed in the second bone 6. When the anchors 40a, 40b are driven into respective anchor holes 74a, 74b, the flexible strands 22a, 22b are captured between the outer surface 52 of the body 42a and the second bone 6. Although embodiments are discussed herein having an interference fixation of the flexible strands 22a, 22b, it will be appreciated that the flexible strands 22a, 22b can be fixed at a selected length using any suitable fixation mechanism, such as an interference fit, a knot, a post, and/or any other suitable fixation between the tissue anchors 40a, 40b and the respective flexible strand 22a, 22b.

The anchoring construct 10 is configured to facilitate soft tissue repair between the first bone 4 and the second bone 6 (i.e., syndesmosis). After an injury, soft tissue can be partially and/or completely disconnected from the first bone 4 and/or the second bone 6. In order to facilitate soft tissue repair, the bone plate 12 is coupled to the first bone using one or more fasteners inserted through fastener holes 20a, 20b defined through the bone plate 12. For example, in some embodiments, one or more screws, pegs, and/or other fasteners are inserted through at least one of the fastener holes 20a, 20b to couple the bone plate 12 to the first bone 4. After coupling the bone plate 12 to the first bone 4, the second end 26 of each of the flexible strands 22a, 22b is coupled to the second bone 6. The flexible strands 22a, 22b can be coupled to the second bone 6 by inserting tissue anchors 40a, 40b into respective anchor holes 74a, 74b formed in the second bone 6. The anchor holes 74a, 74b can be formed prior to and/or simultaneous with insertion of the tissue anchors 40a, 40b. Prior to and/or simultaneous with insertion of the tissue anchors 40a, 40b, an intermediate portion 26c of each of the flexible strands 22a, 22b can be adjusted to position and/or maintain the first bone 4 at a selected spacing with respect to the second bone 6. In some embodiments, the selected spacing facilitates repair and/or reattachment of soft tissue with respect to the first bone 4 and/or the second bone 6.

In some embodiments, the flexible strands 22a, 22b are configured to attach soft tissue to one of the first bone 4 and/or the second bone 6. Prior to insertion of the tissue anchors 40a, 40b into the second bone 6, one or more of the flexible strands 22a, 22b can be passed through and/or otherwise coupled to soft tissue. For example, in various embodiments, one or more of the flexible strands 22a, 22b can be coupled to a ligament, a muscle, connective tissue, and/or other soft tissue. The flexible strands 22a, 22b can be coupled to the soft tissue by a tissue anchor 40a, 40b, by passing the flexible strands 22a, 22b through the soft tissue (for example, with a needle), and/or any other suitable method. In some embodiments, the tissue anchors 40a, 40b are coupled to one of the first bone 4 and/or the second bone 6 to couple the soft tissue to the selected bone 4, 6. The soft tissue can be coupled to the selected bone 4, 6 at a substantially anatomically correct position, although it will be appreciated that soft tissue can be coupled to any suitable position of the selected bone 4, 6 to facilitate repair and/or reattachment of soft tissue.

FIGS. 4-6 illustrate various tissue anchors 40c-40d configured to couple a second end 26b of a respective flexible strand 22a, 22b to a tissue section, such as the second bone 6, in accordance with some embodiments. As illustrated in FIG. 4, in some embodiments, a tissue anchor 40c includes a body 42c defining a channel 44 extending from a first end 46a to a second end 46b. The channel 44 is sized and configured to receive a flexible strand 22c therethrough. The channel 44 can be concentric with the body 42c and/or can be offset with respect to a center of the body 42c. The outer surface 52 of the body 42c can include one or more fixation features 54 configured to couple the tissue anchor 40c to a tissue section. The fixation features 54 can include any suitable features, such as threads, ribs, fins, and/or any other suitable fixation feature.

In some embodiments, a second end 26b of a flexible strand 22c is passed through the passage 44 to form a loop 48 about a portion of the body 42c. The flexible strand 22c is passed into the channel 44 from the first end 46a (and around an upper edge 50a) to the second end 46b. The flexible strand 22c is further passed around a bottom edge 50b of the body 42a. The flexible strand 22c is returned to a first end 46a of the body 42c along an outer surface 52 of the body 42c to form loop 48. In other embodiments, as shown in FIG. 5, the flexible strand 22c is passed from the first end 46a along an outer surface 52 of the body 42c, passed under the bottom edge 50b, and returned to the first end 46a through the channel 44. In this embodiments, no loop is formed in the flexible strand 22c.

As discussed above with respect to FIGS. 1-3, the flexible strand 22c interacts with (e.g., is positioned adjacent to and/or coupled to) a bone plate 12 and/or other anchor at a first end 22a. A length of the intermediate portion 26c of the flexible strand 22c extending between the bone plate 12 and the respective anchor 40c is adjustable by pulling the second end 26b of the flexible strand 22c. As the second end 26b is pulled, the flexible strand 22c advances through the channel 44 and the length of the intermediate portion 26c is reduced, resulting in a corresponding adjustment of the position of the first bone 4 with respect to the second bone 6.

In some embodiments, the upper edge 50a and/or the lower edge 50b of the body 42c are rounded, curved, or smooth to prevent damage to and/or cutting of the flexible strand 22c. For example, in some embodiments, the upper edge 50a is positioned near a first end 46a and defines a first opening of the channel 44 and the lower edge 50b is positioned near a second end 46b and defines a second opening of the channel 44. The first edge 50a and the second edge 50b are rounded, although it will be appreciated that the edges 50a, 50b can have any suitable shape configured to prevent cutting and/or other damage to the flexible strand 22c.

Also as discussed above, the flexible strand 22c can be fixed and/or anchored by an interference fit between an outer surface 52 of the tissue anchor 40c and an inner surface of a respective hole 74a, 74b formed in a bone, such as second bone 6. In some embodiments, the body 42c may include a circumference substantially equal to the circumference of a respective hole 74a, 74b. In other embodiments, the body 42c may include a circumference less than the circumference of a respective hole 74a, 74b. When the anchor 40e is inserted into a selected hole 74a, 74b, the outer surface 52 of the anchor 40c is in contact with the inner surface 72 of the respective hole 74a, 74b and compress a portion of the flexible strand 22c therebetween.

FIG. 6 illustrates a tissue anchor 40d having a protrusion 60 defining an eyelet 62, in accordance with some embodiments. The tissue anchor 40d is similar to the tissue anchors 40a-40c discussed above and similar description is not repeated herein. The protrusion 60 extends from the second end 46b of the body 42d. In some embodiments, the flexible strand 22d can be passed from a first end 46a of the body 42d to a second end 46b along an outer surface 52 and through eyelet 62. The eyelet 62 is sized and configured to receive the flexible strand 22d therethrough. The flexible strand 22d is passed from a first side 64a of the eyelet 62 to a second side 64b and returned to the first side 46a of the tissue anchor 40d along the outer surface 52. The flexible strand 22d is compressed between the outer surface 52 of the anchor 40d and an inner surface of a selected hole 74a, 74b when the anchor 40d is inserted therein. The second end 26b of the flexible strand 22d can be pulled to advance the flexible strand 22d through the eyelet 62 to reduce the length of the intermediate portion 26c of the flexible strand 22d. It should be noted that tissue anchor 40d can be utilized in the embodiments disclosed herein.

Figure 7:
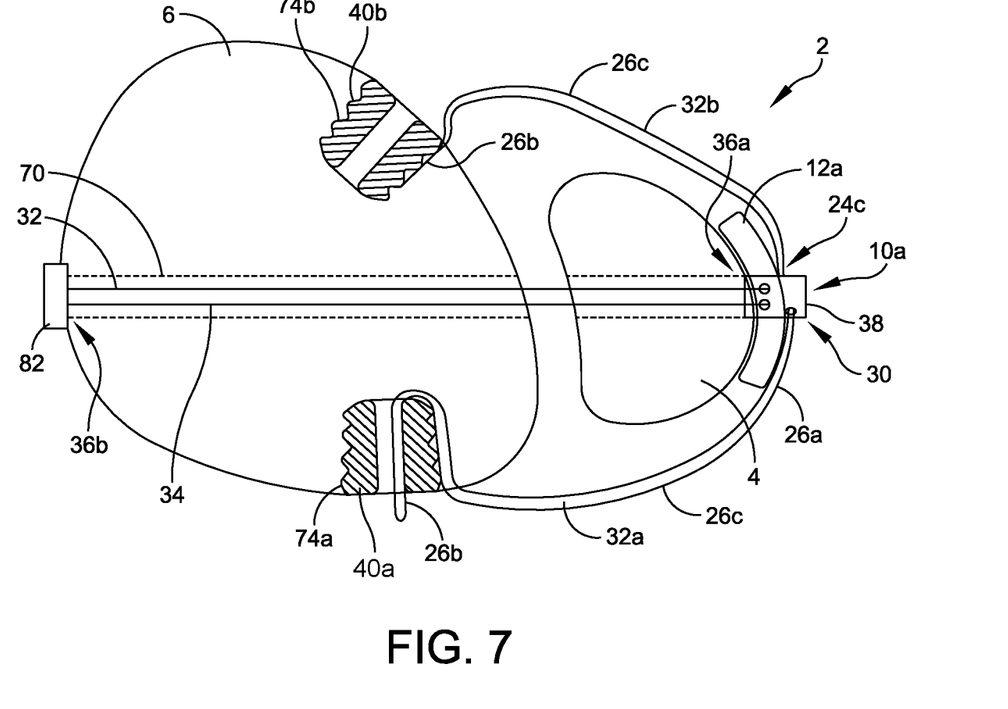
FIG. 7 illustrates an anchoring construct having a flexible construct coupled thereto, in accordance with some embodiments.

FIG. 7 illustrates a cross-section of the first bone 4 and a second bone 6 having an anchoring construct 10a coupled thereto. The anchoring construct 10a is similar to the anchoring construct 10 discussed above, and similar description is not repeated herein. The anchoring construct 10a includes a bone plate 12a coupled to a first bone 4 and a flexible construct 30 configured to maintain the first bone 4 and the second bone 6 at a selected spacing. In some embodiments, the flexible construct 30 includes a primary strand 32 defining at least one adjustable loop 34 extending from a first end 36a to a second end 36b. The adjustable loop 34 is configured to extend through a bone tunnel 70 formed in the first bone 4 and the second bone 6. The primary strand 32 can include any suitable material, such as a suture, ribbon, and/or other suitable material In some embodiments, a first end 36a of the adjustable loop 34 is coupled to the bone plate 12. The first end 36a of adjustable loop 34 can be coupled directly to the bone plate 12 and/or an anchoring element (such as a knot capsule, button, and/or other anchoring element) coupled to the bone plate 12. In the illustrated embodiment, the first end 36a of the adjustable loop 34 is coupled to a knot capsule 38 inserted through a capsule hole 24c defined through the bone plate 12a. A second end 36b of the adjustable loop 34 is coupled to the second bone 6 by a second anchoring element, such as a button 82.

In some embodiments, the knot capsule 38 includes an adjustable knot and/or other fixation mechanism configured to maintain the adjustable loop 34 at a selected length. For example, in some embodiments, the knot capsule 38 includes a slip-knot, such as a prusik knot, configured to lock the adjustable loop 34 at a selected length to maintain a selected syndesmotic spacing between the first bone 4 and the second bone 6. In other embodiments, the capsule anchor 38 can include any suitable locking mechanism for locking the adjustable loop 34 at a selected length. International Patent Application PCT/US2016/066902, filed on Dec. 15, 2016, entitled "Knotless Syndesmosis System" discloses additional details regarding flexible constructs, and is incorporated by reference herein in its entirety.

The adjustable loop 34 can be adjusted to position the first bone 4 and the second bone 6 in a selected spacing. After positioning the first bone 4 and the second bone 6 using the flexible construct 30, a first flexible strand 22a and the second flexible strand 22b can further coupled to the first bone 4 and/or the second bone 6. The flexible strands 22a, 22b each extend from the bone plate 12. The first flexible strand 22a is coupled to the second bone 6 by a first tissue anchor 40a and the second flexible strand 22b is coupled to the second bone 6 by a second tissue anchor 40b. The length of the intermediate portion 26c of the respective flexible strands 22a, 22b extending between the bone plate 12a and the respective anchors 40a, 40b is adjusted prior to and/or simultaneous with implantation of the tissue anchors 40c, 40d to further couple the first bone 4 and the second bone 6. For example, as discussed above, the flexible strands 22a, 22b can be advanced through a channel 44 formed in respective tissue anchors 40a, 40b to decrease the length of the intermediate portion 26c of the respective flexible strands 22a, 22b.

In some embodiments, the first flexible strand 22a and/or the second flexible strand 22b are formed integrally with the primary strand 32 defining the adjustable loop 34. For example, in some embodiments, the primary strand 32 (which defines the adjustable loop 34) includes a first end portion 32a and a second end portion 32b extending from the adjustable loop 32 in the same direction. In some embodiments, the first end portion 32a extends from the knot capsule 38 and is coupled to the first tissue anchor 40a and the second end portion 32b extends from the knot capsule 38 and is coupled to the second tissue anchor 40b. In this embodiment, the first flexible strand 22a and the first end portion 32a are the same and the second flexible strand 22b and the second end portion 32b are the same. The flexible strands 22a, 22b extend from and are formed integrally with the primary strand 32.

In other embodiments, the first flexible strand 22a and/or the second flexible strand 22b can be separate strands coupled to the adjustable loop 34, the knot capsule 38, and/or the bone plate 12. For example, in some embodiments, the first flexible strand 22a and the second flexible strand 22b are independent strands coupled directly to a portion of the bone plate 12 and extending from the bone plate 12 to respective anchors 40a, 40b.

In some embodiments, the end portions 32a, 32b of the primary strand 32 can be pulled to shorten the length of the adjustable loop 34 extending between the knot capsule 38 and the button 82 prior to and/or simultaneous with implantation of the tissue anchors 40a, 40b. For example, in some embodiments, the end portions 32a, 32b are used to adjust the adjustable loop 34 to a selected length to maintain the first bone 4 and the second bone 6 at a selected spacing. Subsequently, the end portions 32a, 32b are coupled to the second bone 6 using respective tissue anchors 40a, 40b. Coupling the end portions 32a, 32b to the second bone 6 provides additional fixation of the first bone 4 and the second bone 6 and/or fixation of soft tissue to the second bone 6.

In some embodiments, coupling the end portions 32a, 32b to the second bone 6 also provides further anchoring the adjustable loop 34 and prevents unwanted lengthening of the adjustable loop 34. For example, in some embodiments, the end portions 32a, 32b are pulled to shorten the adjustable loop 34 to a selected length to maintain the first bone 4 and the second bone 6 at a selected spacing. Each of the end portions 32a, 32b is coupled to the second bone 6 by respective tissue anchors 40a, 40b. The interference fit between the tissue anchors 40a, 40b and respective end portions 32a, 32b maintains the adjustable loop 34 at the selected length.

Figure 8:
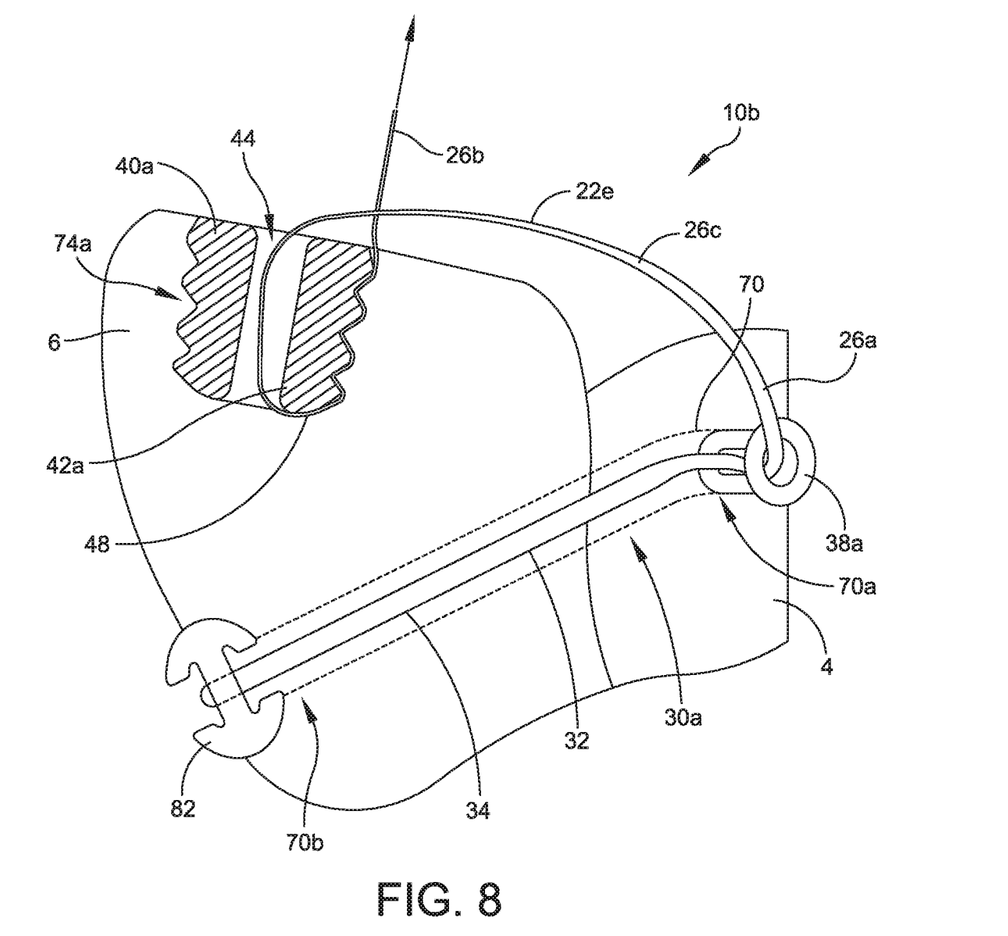
FIG. 8 illustrates an anchoring construct including a knot capsule, in accordance with some embodiments.

FIG. 8 illustrates an anchoring construct 10b including a flexible construct 30a and a flexible strand 22e, in accordance with some embodiments. The anchoring construct 10b is similar to the anchoring construct 10a discussed above but omits the bone plate 12a, and similar description is not repeated herein. The flexible construct 30a includes a knot capsule 38a coupled an adjustable loop 34. The knot capsule 38a is inserted into a first end 70a of the bone tunnel 70 formed through the first bone 4 and the second bone 6. The adjustable loop 34 extends from the knot capsule 38a to a second end 34b. The second end 34b is coupled to the second bone 6 by a button 82 abutting an outer surface of the second bone 6. The flexible construct 30a is similar to the flexible construct 30 discussed above, and similar description is not repeated herein.

In some embodiments, a flexible strand 22e extends from the knot capsule 38a. The flexible strand 22e is coupled to the knot capsule 38a at a first end 26a. The first end 26a can be coupled to any suitable portion of the knot capsule 38a. For example, in some embodiments, the flexible strand 22e is coupled to a knot formed in the knot capsule 38a. In other embodiments, the first adjustable loop 34 is formed of a flexible strand having a first free end. The first free end extends from the knot capsule 38a as the flexible strand 22e. The flexible strand 22e can be formed integrally with the adjustable loop 34 and/or can be a separate flexible strand. The second end 26b of the flexible strand 22e is coupled to a tissue anchor 40a. The tissue anchor 40a is configured couple the second end 26b of the flexible strand 22e to one of a first bone 4 or a second bone 6. The anchoring construct 10b is configured to maintain the first bone 4 and the second bone 6 at a selected spacing and/or to couple soft tissue to the first bone 4 and/or the second bone 6, as discussed above.

Figure 10:
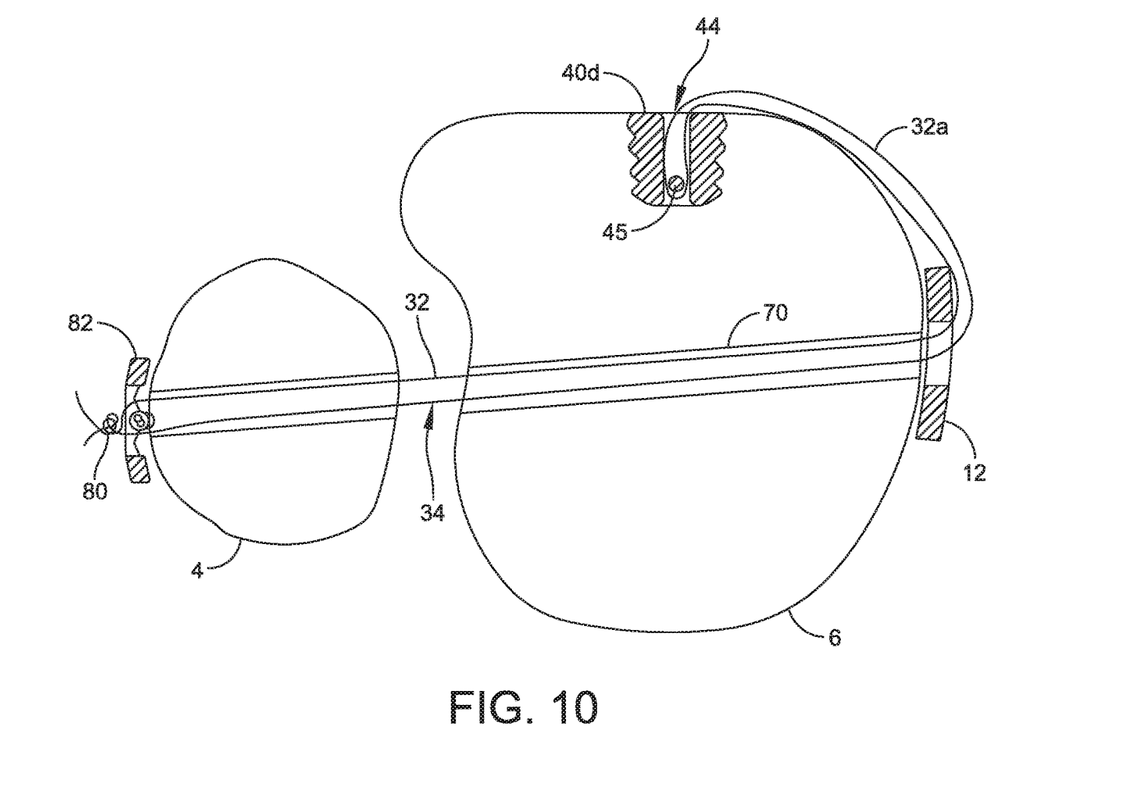
FIG. 10 illustrates an anchoring construct including an anchor having an internal peg, in accordance with some embodiments.

FIG. 10 illustrates an anchoring construct 10c including a tissue anchor 40d having an internal peg 45, in accordance with some embodiments. The anchoring construct 10c is similar to the anchoring construct 10b discussed above, and similar description is not repeated herein. In the illustrated embodiment, the anchoring construct 10c includes a tissue anchor 40d having a first end 34a of an adjustable loop 34 coupled thereto. The tissue anchor 40d is sized and configured to be passed through a fastener hole 20a formed in the bone plate 12. The tissue anchor 40d is passed through the fastener hole 20a such that the adjustable loop 34 extends through the fastener hole 20a. The tissue anchor 40d is coupled to a second bone 6.

In some embodiments, the tissue anchor 40d includes an internal channel 44 and a peg 45 extending through the internal channel 44. The primary strand 32 of the adjustable loop 34 is passed around the peg 45 to couple the adjustable loop 34 to the tissue anchor 40d. In some embodiments, the peg 45 enables the adjustable loop 34 to the tightened and/or loosened after installation of the tissue anchor 40d in the second bone 6, as discussed in greater detail below. In some embodiments, the tissue anchor 40d includes an internal locking mechanism (not shown) configured to prevent the adjustable loop 34 from loosening after being tightened.

In some embodiments, the adjustable loop 34 extends through a bone tunnel 70 formed in the first bone 4 and the second bone 6. A second end 34b of the adjustable loop 34 is coupled to an anchor, such as a button 82, positioned against the first bone 4. Although embodiments are illustrated including a button 82, it will be appreciated that the anchor can include one or more of a button, a knot capsule, a bone plate, and/or any other suitable structure. The adjustable loop 34 defines a knot 80, such as a self-tightening knot, configured to tighten and/or loosen the adjustable loop 34. The adjustable loop 34 can be shortened to position the first bone 4 and the second bone 6 at a predetermined spacing. In some embodiments, the adjustable loop 34 is positioned within a knot capsule (not shown) including one or more features configured to tighten and/or maintain the knot 80 and/or the adjustable loop 34.

Figure 9:
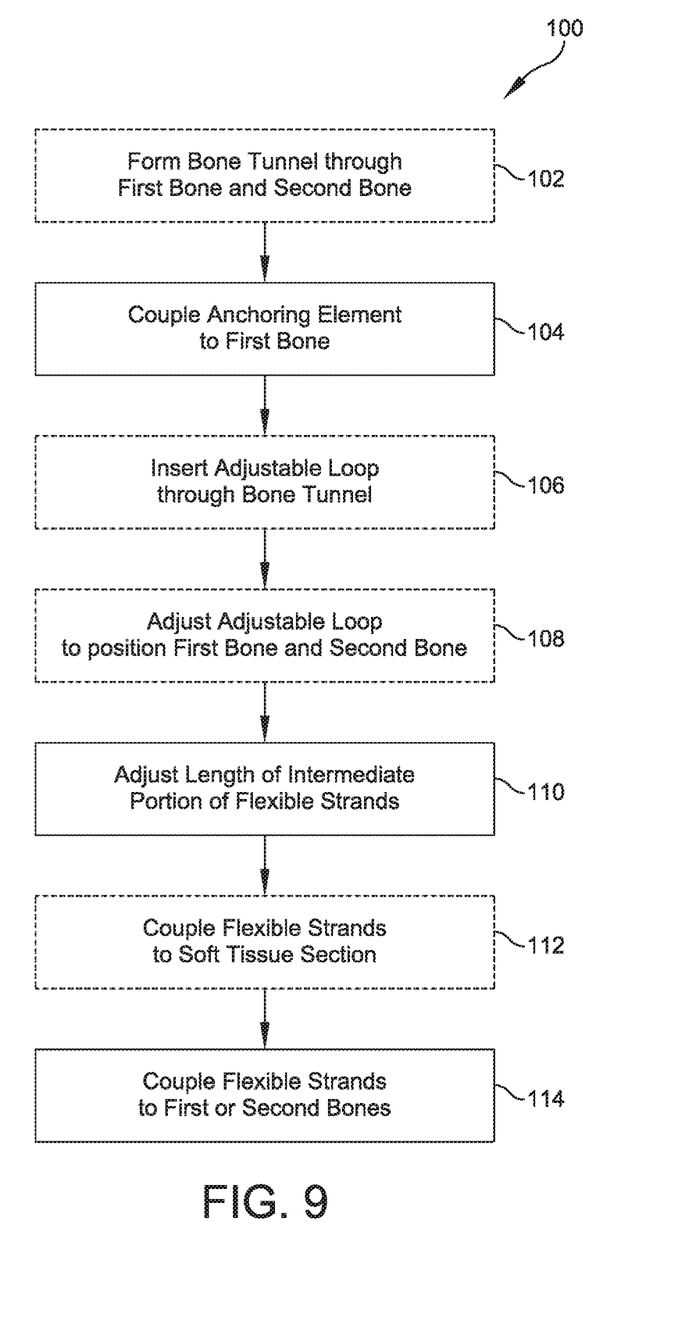
FIG. 9 illustrates a method of syndesmosis, in accordance with some embodiments.

FIG. 9 illustrates a method of syndesmosis 100, in accordance with some embodiments. With reference to FIGS. 1-9, the method 100 is discussed. At optional step 102, a bone tunnel 70 is formed through a first bone 4 and a second bone 6. The bone tunnel 70 extends from a first side of the first bone 4 to a second side of a second bone 6. The bone tunnel 70 is sized and configured to receive an adjustable loop 34 therethrough.

At step 104, an anchoring element, such as a bone plate 12 or a knot capsule 38, is coupled to the first bone 4. In some embodiments, the bone plate 12 is coupled to the first bone 4 by inserting one or more fasteners through fastener holes 20a, 20b formed in the bone plate 12. The fasteners can be any suitable fasteners, such as a screw, a pin, and/or any other suitable fixation element. In other embodiments, a knot capsule 38 can be coupled directly to the first bone 4, for example, by inserting the knot capsule 38 at least partially into the bone tunnel 70. The bone plate 12 and/or the knot capsule 38 can include at least one flexible strand 22a, 22b extending therefrom.

At optional step 106, an adjustable loop 34 of a flexible construct 30 is inserted through the bone tunnel 70 and coupled to the first bone 4 and/or the second bone 6. The adjustable loop 34 can be inserted through the bone tunnel 70 using any suitable mechanism, such as, for example, a needle coupled to a pull strand inserted through the bone tunnel 70, although it will be appreciated that any suitable insertion mechanism can be used. The adjustable loop 34 can be coupled to the first bone 4 using any suitable anchor, such as the knot capsule 38, a button, and/or any other suitable anchor. In some embodiments, the adjustable loop 34 is coupled to the first bone 4 prior to, simultaneous with, and/or after coupling the bone plate 12 and/or knot capsule 38 to the first bone. In some embodiments, second end 36b of the adjustable loop 34 is coupled to the second bone using a button 82. The adjustable loop 34 and/or the knot capsule 38 can be inserted through a capsule hole 20c defined through the bone plate 12.

At optional step 108, the adjustable loop 34 is adjusted to maintain the first bone 4 and the second bone 6 at a selected spacing. For example, in some embodiments, one or more free ends extending from the adjustable loop 34 can be pulled to adjust the length of the adjustable loop 34. The adjustable loop 34 is shortened to position the first bone 4 and the second bone 6 at the selected spacing. In some embodiments, the adjustable loop 34 can be locked at a selected length using any suitable mechanism, such as, for example, a self-tightening knot positioned within a knot capsule 38.

At step 110, a length of an intermediate portion 26c of each of flexible strands 22a, 22b is adjusted. The flexible strands 22a, 22b extend from the bone plate 12 and/or the knot capsule 38. In some embodiments, the flexible strands 22a, 22b extend from the adjustable loop 34. The intermediate length 26c of a respective flexible strand 22a, 22b is adjusted by advancing the flexible strand 22a, 22b through a portion of the respective tissue anchor 40a, 40b. For example, in various embodiments, the flexible strands 22a, 22b can be advanced through a channel 44 and/or an eyelet 62 defined by the anchor 40a, 40b to shorten the intermediate length 26c of the respective flexible strand 22a, 22b. In some embodiments, each of the flexible strands 22a, 22b define a loop 48 around a portion of a respective tissue anchor 40a, 40b. The second end 26b of the flexible strand 22a, 22b is pulled to decrease the length of the intermediate portion 26c.

At option step 112, one or more of the flexible strands 22a, 22b is coupled to a soft tissue section. The soft tissue section can include any suitable soft tissue, such as connective tissue, ligaments, muscle, etc. The soft tissue can be coupled to the flexible strands 22a, 22b by a respective tissue anchor 40a, 40b and/or by passing the flexible strands 22a, 22b through the soft tissue.

At step 114, one or more flexible strands 22a, 22b are coupled to the one of the first bone 4 and/or the second bone 6. The flexible strands 22a, 22b are coupled to a selected bone 4, 6 by a respective tissue anchor 40a, 40b coupled to a second end 26b of the flexible strand 22a, 22b. In some embodiments, the length of an intermediate portion 26c of one or more flexible strands 22a, 22b is fixed by an interference fit between an outer surface 52 of a respective anchor 40a, 40b and an inner surface 72 of a respective anchor hole 74a, 74b formed in the second bone 6. The flexible strand 22a, 22b is wedged between the anchor 40a, 40b and the inner surface of the respective anchor hole 74a, 74b.

Although the subject matter has been described in terms of exemplary embodiments, it is not limited thereto. Rather, the appended claims should be construed broadly, to include other variants and embodiments, which may be made by those skilled in the art.

What is claimed is:

1. An anchoring system, comprising:
   an anchoring construct, including:
   a first anchor having a body defining a first side and a second side;
   a second anchor; and
   a first flexible strand defining an adjustable loop extending between the first side of the first anchor and the second anchor, the first flexible strand having a first end extending from the second side of the first anchor; and
   a tissue anchor coupled the first end of the first flexible strand and configured to couple the first end of the first flexible strand to a first tissue section, wherein the tissue anchor and the first end of the first flexible strand are configured to maintain the adjustable loop at a predetermined length between the first anchor and the second anchor.

2. The system of claim 1, wherein the first end of the first flexible strand is configured to be coupled to the tissue section by an interference fit.

3. The system of claim 2, wherein the tissue anchor comprises a body defining a channel, and wherein the first flexible strand extends at least partially into the channel.

4. The system of claim 3, wherein the first flexible strand defines a loop about a portion of the body of the tissue anchor.

5. The system of claim 1, comprising a bone plate having a body extending between a bone facing surface and an opposing surface, the body defining a hole therethrough, wherein the first anchor and the first flexible strand of the anchoring construct are sized and configured for insertion through the hole defined in the body.

6. The system of claim 5, comprising a second flexible strand coupled to the bone plate and a second tissue anchor coupled to a first end of the second flexible strand.

7. The system of claim 1, wherein the first anchor is selected from the group consisting of a knot capsule, a bone plate, a tissue anchor, and a button.

8. The system of claim 1, wherein the second anchor is selected from the group consisting of a knot capsule, a bone plate, a tissue anchor, and a button.

9. A system, comprising:
   a bone plate having a body extending between a bone facing surface and an opposing surface, the body defining a hole therethrough sized and configured to receive a portion of a flexible construct therethrough;
   a flexible strand defining an adjustable loop extending between the bone facing surface of the bone plate and an anchor, the flexible strand having a first end extending from the opposing side of the bone plate; and
   a tissue anchor coupled to the first end of the flexible strand, wherein the tissue anchor is configured to couple the flexible strand to a tissue section to maintain the adjustable loop at a predetermined length between the bone plate and the anchor.

10. The system of claim 9, wherein the tissue anchor comprises a body defining a channel extending from a first end to a second end of the body, wherein the flexible strand extends from the first end of the body through the channel to the second end, around the second end of the body, and returns to the first end of the body along an outer surface of the body to define a loop.

* * * * *